US008470584B2

(12) United States Patent
Bayless et al.

(10) Patent No.: US 8,470,584 B2
(45) Date of Patent: Jun. 25, 2013

(54) APPARATUS AND METHOD FOR GROWING BIOLOGICAL ORGANISMS FOR FUEL AND OTHER PURPOSES

(75) Inventors: David J. Bayless, Athens, OH (US); Morgan Lefay Vis-Chiasson, Athens, OH (US); Ben Stuart, Athens, OH (US); Gregory G. Kremer, Athens, OH (US)

(73) Assignee: Ohio University, Athens, OH (US)

( * ) Notice: Subject to any disclaimer, the term of this patent is extended or adjusted under 35 U.S.C. 154(b) by 577 days.

(21) Appl. No.: 11/746,389

(22) Filed: May 9, 2007

(65) Prior Publication Data

US 2007/0264708 A1 Nov. 15, 2007

Related U.S. Application Data

(60) Provisional application No. 60/799,440, filed on May 10, 2006.

(51) Int. Cl.
*C12N 1/12* (2006.01)
*C12M 1/00* (2006.01)

(52) U.S. Cl.
USPC .................. 435/257.1; 435/292.1; 47/1.4

(58) Field of Classification Search
USPC ............ 435/257.1, 292.1, 262.5, 264; 47/1.4; 362/554, 556, 558, 532, 563
See application file for complete search history.

(56) References Cited

U.S. PATENT DOCUMENTS

| | | | |
|---|---|---|---|
| 6,083,740 A | 7/2000 | Kodo et al. | |
| 6,156,561 A | 12/2000 | Kodo et al. | |
| 6,209,855 B1 | 4/2001 | Glassford | |
| 6,667,171 B2 | 12/2003 | Bayless et al. | |
| 7,537,200 B2 | 5/2009 | Glassford | |
| 2005/0239197 A1 | 10/2005 | Katerkamp et al. | |
| 2009/0047722 A1* | 2/2009 | Wilkerson et al. | 435/173.7 |

FOREIGN PATENT DOCUMENTS

| | | |
|---|---|---|
| GB | 1509630 | 4/1978 |
| JP | 05-064577 | 3/1993 |

OTHER PUBLICATIONS

Jin-Young An and Byung-Woo Kim. "Biological desulfurization in an optical-fiber photobioreactor using an automatic sunlight collection system". Elsevier. Journal of Biotechnology vol. 80, pp. 35-44, 2000.*

* cited by examiner

*Primary Examiner* — Michael Hobbs
(74) *Attorney, Agent, or Firm* — Jason H. Foster; Kremblas & Foster (57) ABSTRACT

A bioreactor apparatus in which a container has sidewalls, a floor and a ceiling defining a chamber that contains a slurry of water, nutrients and photosynthetic microorganisms. A plurality of optical fibers, each of which has a first end disposed outside the chamber and a second end in the mixture. A light collector spaced from the container has light incident on it and focuses the light onto the first ends of the plurality of optical fibers, thereby permitting the light to be conveyed into the mixture to promote photosynthesis. At least one nozzle is in fluid communication with a source of gas, such as exhaust gas from a fossil-fuel burning power plant containing carbon dioxide. The nozzle is disposed in the mixture beneath the second ends of the optical fibers for injecting the gas into the mixture.

12 Claims, 6 Drawing Sheets

APPARATUS AND METHOD FOR GROWING BIOLOGICAL ORGANISMS FOR FUEL AND OTHER PURPOSES

BACKGROUND OF THE INVENTION

1. Field of the Invention

This invention relates to an apparatus and a method for growing photosynthetic microorganisms, possibly from exhaust gas containing carbon dioxide.

2. Description of the Related Art

It is well known that fossil fuels, such as petroleum-derived fuels and coal, are limited in supply. Additionally, the combustion of such fuels contributes substantial carbon to the atmosphere. The release of carbon long stored in such fuels is the subject of global concern relating to climate change and other environmental problems. Nevertheless, fossil fuels are the largest fuel source for automobiles and energy production facilities.

Biofuels are derived from recently living organisms or their metabolic byproducts, but contain different hydrogen and carbon containing molecules than fossil fuels. Biofuels contain sufficient enthalpy to compete with fossil fuels for vehicle fuel and energy production. Most biofuels are considered neutral in their release of carbon into the atmosphere, because the living organisms remove carbon from the air, but that carbon is subsequently released during the chemical reaction that produces work from the stored solar energy.

Biofuels are a renewable energy source, unlike other natural resources such as petroleum, coal, and nuclear fuels. Some biofuels can be grown in a conventional setting, such as a farm field, while others must be grown in unique, controlled settings. A bioreactor is a vessel in which a chemical process is carried out that involves organisms or biochemically active substances derived from such organisms. Known bioreactors take the exhaust gases of, for example, fossil fuel burning power plants, and use the $CO_2$ therein to "fuel" growth of microalgae and other photosynthetic microorganisms. Such bioreactors prevent carbon from the exhaust gas stream from being released into the air, and produce biofuel therefrom that provides additional energy. Open-pond bioreactor systems have existed for some time, but are unsuitable in many ways, especially for large sources of $CO_2$.

Microalgae have much faster growth-rates than terrestrial crops. Depending on the bioreactor and the strain, the per unit area yield of oil from algae is estimated to be many times greater than the next best crop, which is palm oil. Algal-oil processes into biodiesel as easily as oil derived from land-based crops. The difficulties in efficient biodiesel production from algae lie in finding a cost-effective bioreactor that is best suited to a strain of algae that contains sufficient lipids.

Research into algae for the mass-production of fuel is mainly focused on microalgae, as opposed to macroalgae (seaweed). Microalgae are organisms capable of photosynthesis that are less than 2 mm in diameter. These include the diatoms and cyanobacteria. This preference towards microalgae is due largely to its less complex structure, fast growth rate, and high oil content in some species.

Despite the scientific advantages of biofuels and the availability of bioreactors that are capable of producing such fuels, economic disadvantages have restricted the extent to which bioreactors have been implemented. For example, one disadvantage of conventional bioreactors is the fact that they become economically feasible only when natural light is used. The ability to expose microorganisms to sufficient natural light is a function of the exposed surface area of conventional bioreactors. Space is not always available where large supplies of $CO_2$ are being produced. Biofuels produced from such bioreactors can only compete with petroleum-based fuels if their production is high enough that economies of scale exist. This is difficult with conventional bioreactors.

Therefore, the need exists for a bioreactor that makes carbon removal and biofuel production economically feasible enough that it will be adopted by the energy producing industry.

BRIEF SUMMARY OF THE INVENTION

The production of microalgae as a feedstock for refining into biodiesel requires bioreactors that are capable of maximum productivity in minimum space and with minimal artificial light and other energy inputs. Current bioreactor designs are limited to operation during sunlight hours, primarily because their design is entirely predicated on getting light from the outside and having it penetrate by transmission through transparent walls to the algae. A simple economic analysis shows that use of only artificial light is too expensive. However, by not having production during the nighttime hours when no available solar energy, significant productivity is lost.

The bioreactor of the invention addresses significant problems of conventional bioreactor designs. First, the invention uses solar collecting and transmitting features so that photosynthetically active radiation can be delivered to the microalgae at optimal levels. Second, the invention uses a fiber hanger so that light transmission fibers are terminated inside the bioreactor, thereby providing the direct application of light without a separate distribution system. Third, the invention uses an algal slurry to increase productivity over a biofilm system. The circulating slurry uses transport processes to create dark zones that are internal to the bioreactor to provide time for dark reactions, and thus potentially greatly increasing algal productivity. Finally, the light transmission and distribution system permits the bioreactor to be built in the vertical direction, thereby decreasing the structure's space consumption over a pond or raceway cultivator.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose. For example, the word connected or term similar thereto are often used. They are not limited to direct connection, but include connection through other elements where such connection is recognized as being equivalent by those skilled in the art.

DETAILED DESCRIPTION OF THE INVENTION

Figure 1:
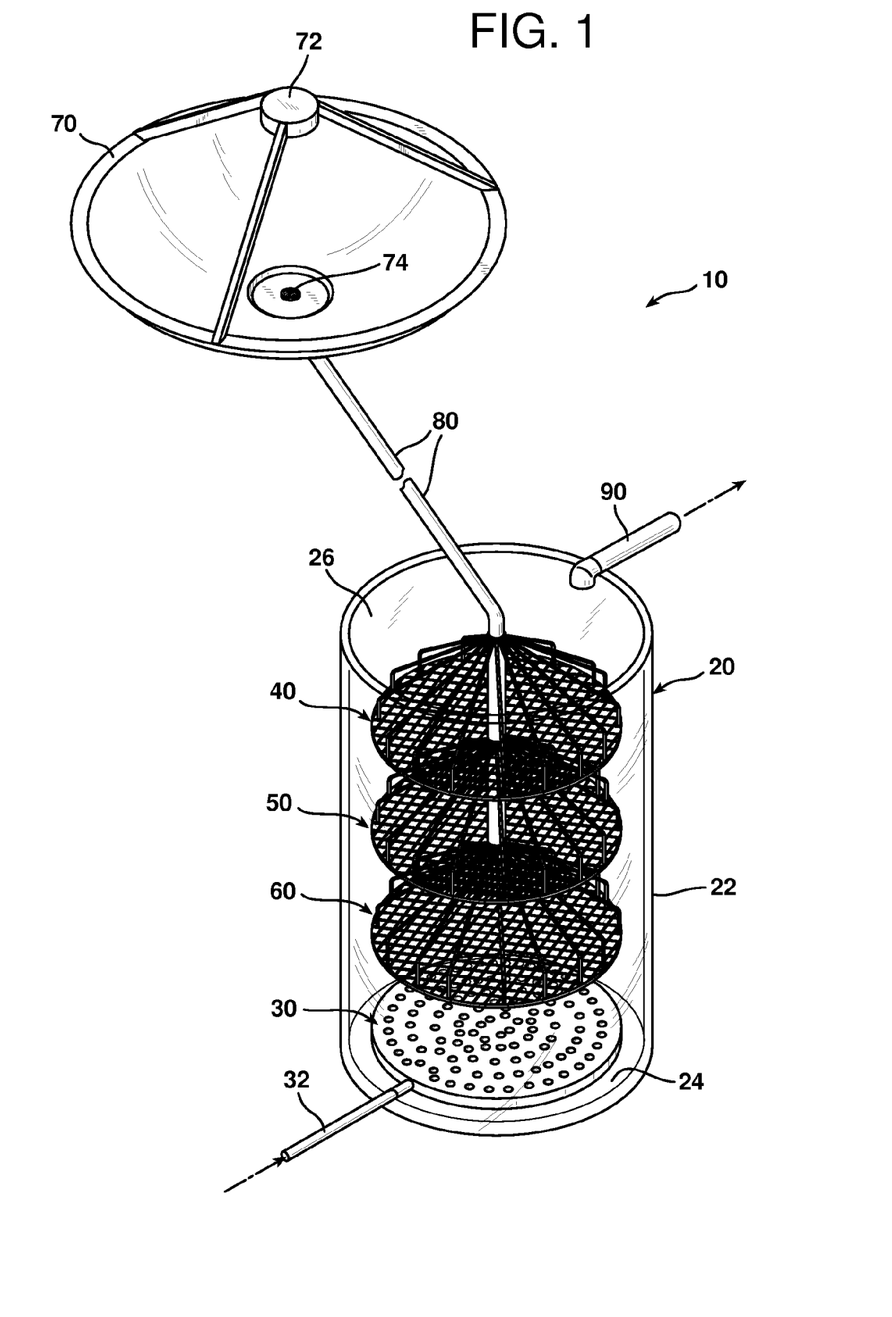
FIG. 1 is a view in perspective illustrating a preferred embodiment of the present invention.

The preferred embodiment of the present invention is shown in FIG. 1, in which the bioreactor 10 is shown in a preferred configuration. The container 20 is a cylindrical tube having a sidewall 22 a floor 24 and a ceiling 26. The container 20 is preferably approximately four inches in diameter, and approximately seven feet tall. The container 20 is can be made of a plastic material, such as transparent acrylic or polycarbonate, or it can be made of an opaque metal or other material. The container 20 does not have to be transparent, but it can be. It will become apparent that the material of which the container 20 is made must be strong enough to contain a water and algae mixture, but need not have light-transmission characteristics, even though such characteristics are contemplated. Of course, composites, ceramics and other plastics are contemplated for the material of which the container 20 is made. The container 20 defines a chamber that is preferably substantially full of water and microorganisms in a slurry. Other materials, such as nutrients, and contaminants can be in the container 20, but these comprise a small fraction of the contents of the container 20.

At or near the floor 24 of the container 20, a nozzle 30 is fixed in place, preferably by attachment to the floor 24, or by a rigid connection to the conduit 32. The conduit 32 is preferably a tube that extends through the sidewall 22 of the container 20 at an air-tight and water-tight seal. The conduit 32 is in fluid communication with a source of fluid, preferably a gas, such as $CO_2$, either in pure form or in a mixture. The source of gas is preferably at high pressure, and the gas is conveyed into the nozzle 30 through the conduit 32 to be injected out of the nozzle 30 into the fluid contained in the container 20. This is described in more detail below. The interior of the conduit 32 is preferably in fluid communication with the container 20, unless a valve (not shown) is interposed therebetween to limit the amount of gas that can flow into the container 20.

The nozzle 30 preferably has a plurality of openings through which the gas escapes the nozzle 30 and enters the container 20. These openings are preferably distributed, as shown, around the nozzle 30 to distribute gas around the entire cross-sectional area of the container 20.

The light distributors 40, 50 and 60 are mounted in the container 20 at spaced intervals along the height of the container 20. The distributors are preferably mounted to the sidewall 22, such as by adhesive or fasteners, such as screws. Of course, any suitable fastener can be used. It is preferred that the distributors 40-60 be spaced approximately at 24 inch intervals along the height of the container 20, although this distance can vary, depending upon the dimensions and the fluid dynamics of the system. The distributor 60 is preferably about 12 inches above the nozzle 30, although this distance can be varied for a system of a different size.

The light collector 70 has a primary collection mirror that directs incident light, such as sunlight, onto a reflector 72 that reflects the light onto the end 74 of a bundle of optical fibers 80. The optical fibers 80 extend into the container 20, which is spaced from the container 20, and preferably extends through a water and air-tight seal. The fibers 80 are divided into smaller clusters, each of which extends to one of the light distributors 40, 50 and 60, as described further below. Each fiber may be a conventional optical fiber, such as a 3.0 millimeter diameter glass fiber.

The light collector 70 is preferably spaced from the container 20 and mounted on the exterior of a building or other structure, such as the building housing the container 20. The collector 70 can thus collect solar radiation and focus it onto the fibers 80 so that the radiation can be transmitted to the interior of the container 20. The dish 70 preferably is controlled to move throughout the day to follow the path of the sun in a conventional manner in order to maximize the amount of natural light incident thereon. One type of light collector that is contemplated for use is sold under the name Solar Tracker by Sunlight Direct. Of course, other conventional light collectors can be substituted for the light collector 70. The critical feature is to concentrate photons in the visible spectrum onto the fibers.

The gas outlet 90 is mounted in the ceiling 26 of the container 20 at an air and water-tight seal. The gas outlet 90 permits gas that flows into the container 20 through the conduit 32 to flow out of the container 20. The preferred container 20 has one inlet (conduit 32) and one outlet (outlet 90) for any fluid. Otherwise, the container 20 is preferably impermeable to any gas or liquid.

Figure 2:
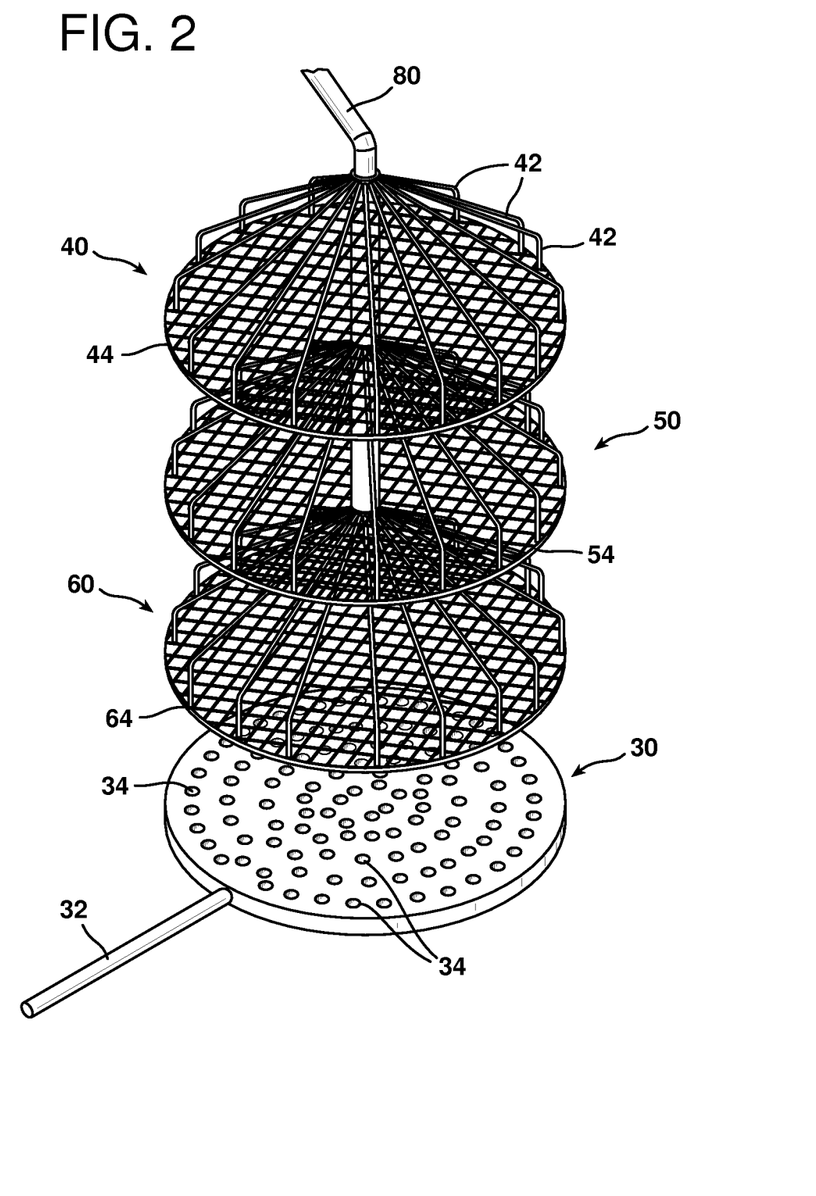
FIG. 2 is a view in perspective illustrating an exploded view of a preferred interior components of the preferred embodiment of FIG. 1.
Figure 3:
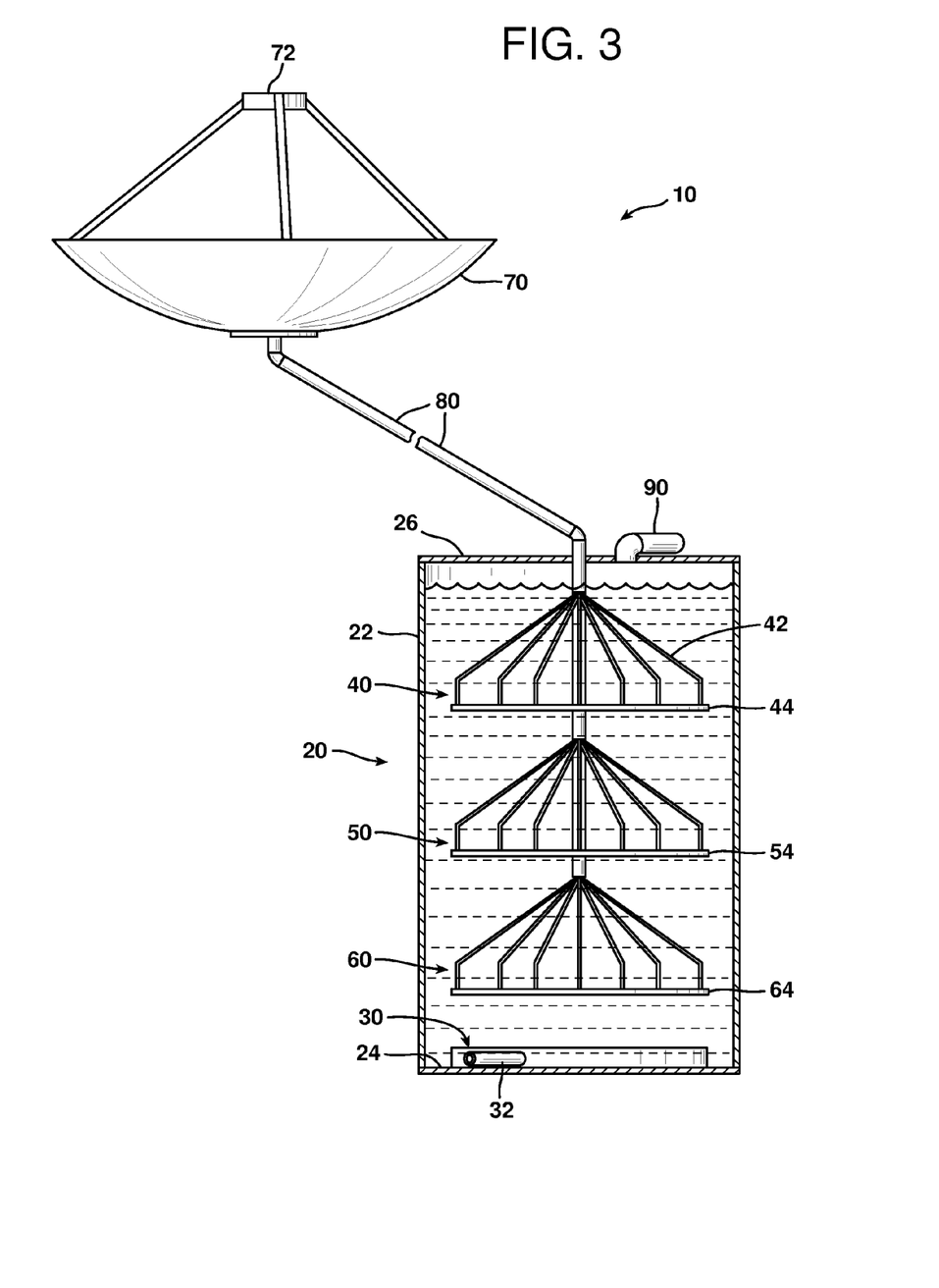
FIG. 3 is a side view illustrating the embodiment of FIG. 1.
Figure 4:
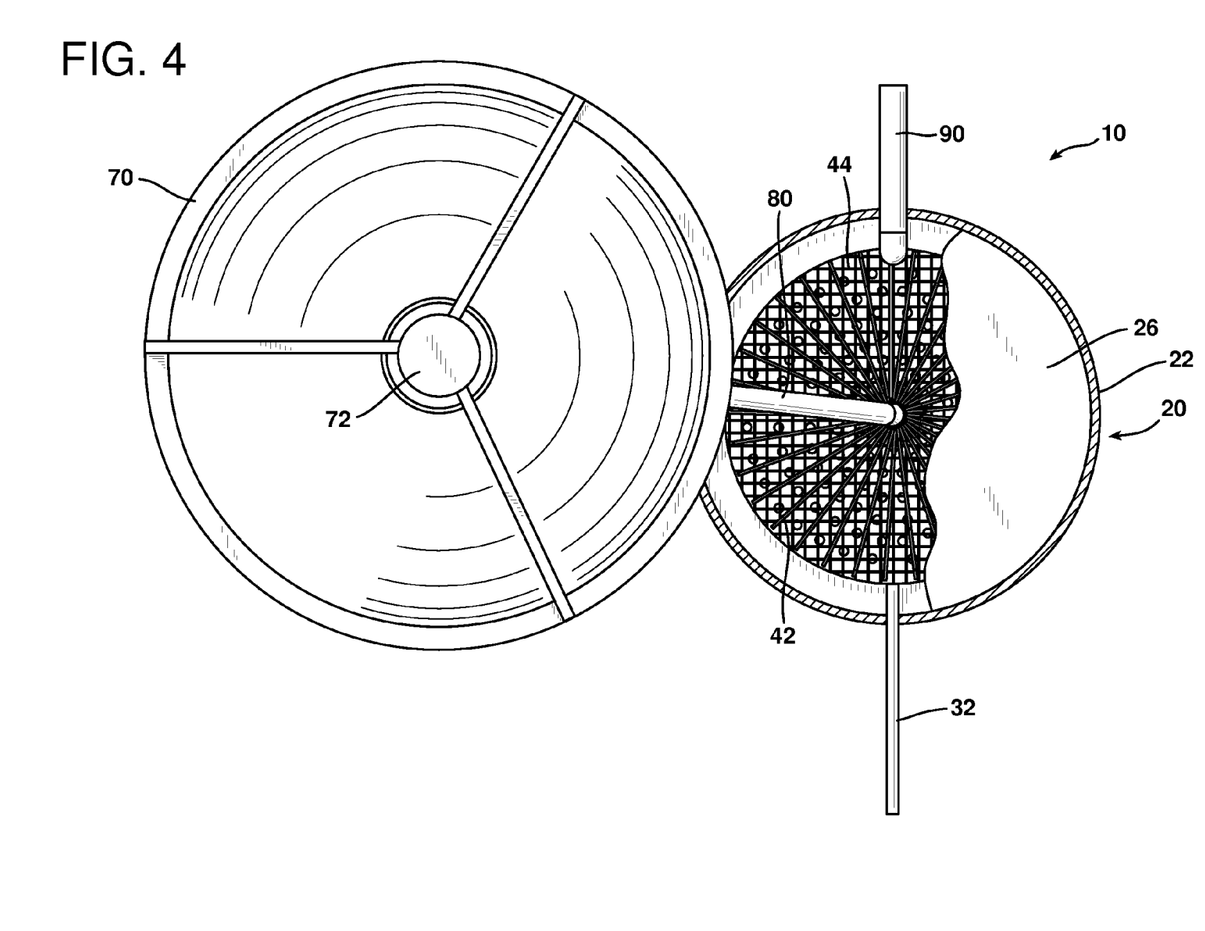
FIG. 4 is a top view illustrating the embodiment of FIG. 1.

The light distributors 40, 50 and 60 are shown in detail in FIG. 2, which makes it apparent that the distributors are substantially identical. Therefore, only the distributor 40 will be described, and the description thereof applies substantially to the distributors 50 and 60.

Figure 6:
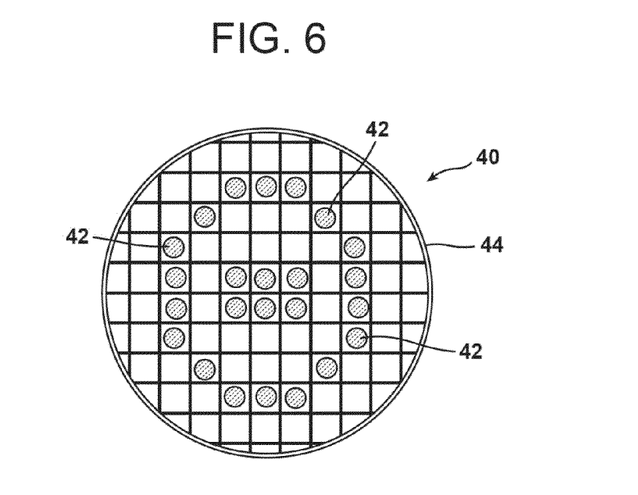
FIG. 6 is a top view in section illustrating an optical fiber hanger.

One cluster of fibers from the bundle of fibers 80 extends to the light distributor 40. Each of the fibers 42 in that cluster is spaced from every other fiber in the cluster, as illustrated in FIG. 2, around the hanger 44 that supports the fibers in this configuration. The fibers 42 can also be inserted in the central region of the hanger, as illustrated in FIG. 6. The hanger 44 is preferably a nylon mesh netting with apertures through which the fibers extend and are maintained by friction, and by the fact that the fibers are so rigid that bending is insufficient to displace the fibers axially out of the apertures. The fibers preferably extend below the hanger 44 so that as water circulates around the fiber tips, the fibers bend and are displaced radially. This radial movement due to water circulation, and impact with other fibers and the container sidewall 22, aids in cleaning the fiber tips where the light beam exits and where algae otherwise collect and attach. There are many structures that can maintain the fibers in the desired spaced configuration, including clamps, brackets and screens, which the person having ordinary skill will recognize from the description herein, and which are too numerous to list.

The light distributor 50 has a different cluster of fibers from the bundle of fibers 80, and these are attached to the hanger 54 in a substantially similar manner. The hanger 64 of the light distributor 60 receives and mounts the third different cluster of fibers in a similar manner. With the present invention, each of the light distributors 40, 50 and 60 has a unique cluster of optical fibers, with ends spaced axially from each other, through which solar radiation is conveyed from the collector 70 to the interior of the container 20 and to the fibers maintained at each respective hanger.

The nozzle 30 mounts beneath the distributors, and gas enters the nozzle 30 by the conduit 32 as noted above. The gas preferably contains $CO_2$, but can be any gas. The gas is preferably supplied by the exhaust from fossil fuel combustion, such as a coal-burning power plant, natural gas burning power plant, gasoline internal combustion engine, a water gas shift reactor or any other carbon-laden gas producing apparatus. Alternatively, the source of gas can be any apparatus that produces gas containing elements and/or compounds that can be utilized by photosynthetic microorganisms. The gas entering the nozzle 30 exits the same and enters the water in the container 20 through the openings 34 at high pressure, thereby forming many small bubbles and creating turbulence in the water in the container 20. This turbulence stirs the water and algae mixture, thereby causing many of the algae to pass near the ends of the optical fibers.

Figure 5:
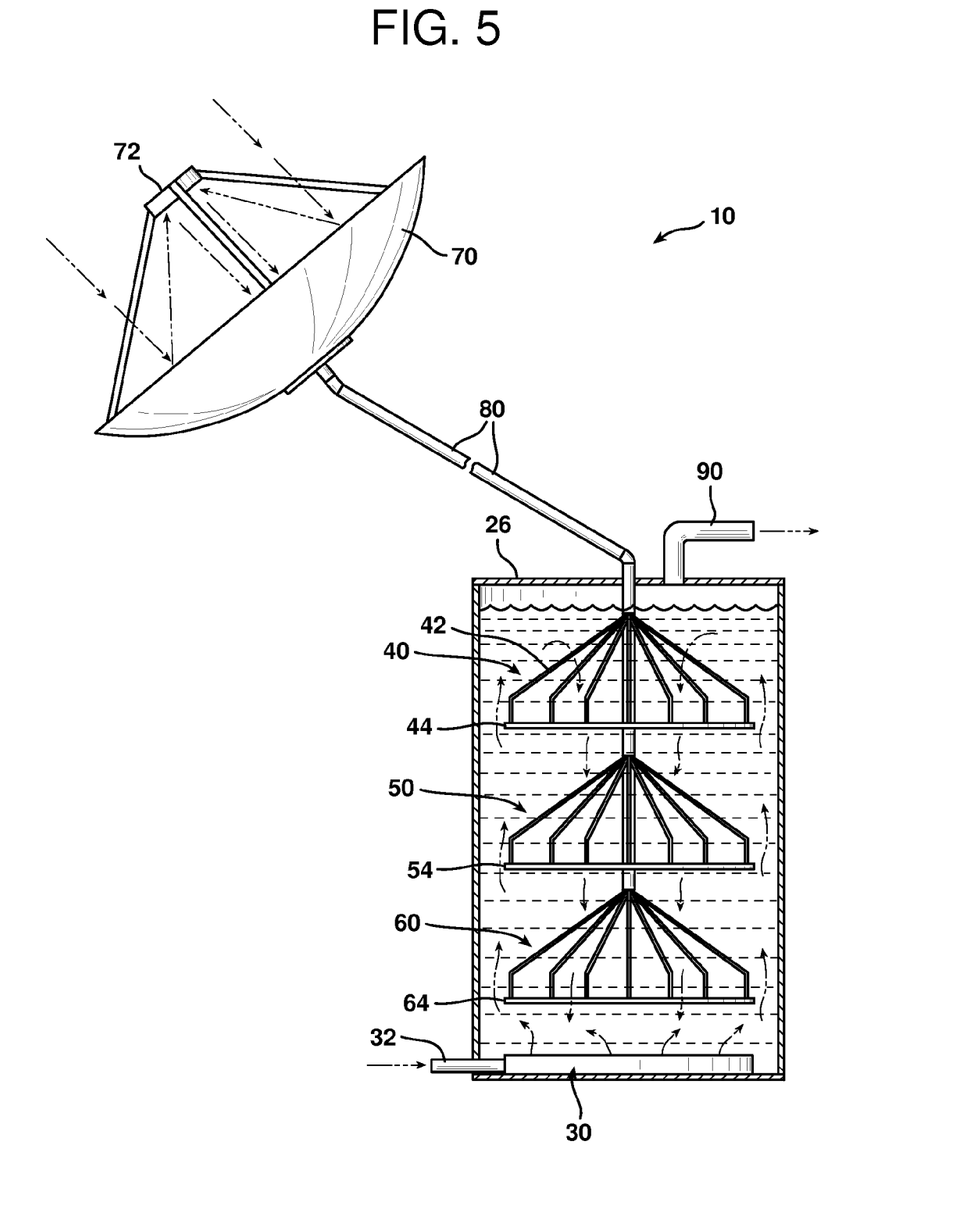
FIG. 5 is a side view illustrating the embodiment of FIG. 1.

Of course, other nozzles are contemplated as substituting for the nozzle 30 illustrated. For example, although the nozzle 30 has many openings that are directed upwardly, nozzles are contemplated that have more openings. Nozzles with fewer openings, such as only around the perimeter of the container 20 as shown in FIG. 5, can also be used. Indeed, even a few openings or a single opening could substitute for the preferred nozzle 30. The nozzle openings can also be oriented to inject gas into the water at a horizontal angle to the axis of the container, such as 45 degrees, and nozzle openings can inject gas at a vertical angle to the axis. Such angled nozzles can encourage helical or other advantageous circulation of the water/algae mixture.

By moving briefly past the ends of the optical fibers, the algae is exposed to light, which causes photosynthetic growth. Additionally, because the algae dwell near the light for a short period, such as about a fraction of a second, and then pass away from the light, the algae is exposed to a light and dark cycle, which further enhances growth of the algae. By circulating the water/algae mixture using carbon dioxide ($CO_2$) gas that the algae absorb, growth of the algae is enhanced.

Circulation of the water/algae mixture also causes the fibers to move radially (laterally) outwardly and inwardly relative to their contact point with their respective hangers. This movement "washes" the tips of the fibers, which is preferably the only part through which light passes into the container 20, and keeps the tips clean. The movement also permits the tips to contact other fibers and the sidewall 22 of the container 20 to further clean the fiber tips.

Because algae convert $CO_2$ to $O_2$ in the photosynthesis process, the gas that exits the container 20 through the outlet 90 preferably contains little or substantially no carbon. Instead, the algae use the carbon in their normal respiration to grow, thereby depleting the gas of the ingredient that is desirably sequestered from gas released into the atmosphere. The gas from the outlet 90, if it contains $CO_2$, can be further treated to remove $CO_2$ or other pollutants, or it can be released into the atmosphere if permitted. Indeed, the container 20 can be part of a recycling system in which a gas is converted in large volumes to a more desirable gas or gases.

Thus, the invention includes a bubble-column bioreactor in which the gas flows from a bottom header, where it is injected into the slurry of water and algae, to the top, where it is separated from the liquid and exits the container. The liquid slurry is fluidized by the motion of the gas, and is circulated to enhance the extent to which the algae are exposed to light-dark cycles. Pumping can be used to flow the slurry from top to bottom in a counter-flow manner to the gas to recirculate the slurry.

The flow of algal suspension is carried over regions of fiber bundles, which are secured at fixed locations in the bioreactor by the hangers. The fibers terminate at about the height of the hanger and emit the photosynthetically active radiation to the slurry. As the algae move past the hangers, they move into darker regions, thereby promoting the dark cycle reactions, which may be shorter than one second in duration. The algal slurry's continuous motion toward and away from the light sources stimulates photosynthesis, ensures nutrient transport within the bioreactor and keeps the fiber ends free of algal buildup.

The light delivered to the fibers 80 comes from two likely sources. The first and primary source is one or more tracking mirrors as described above. An alternative design for these mirrors is a trough-like arrangement, with a primary trough focusing light onto a secondary mirror that focuses light on the fibers 80. The trough is able to track the sun throughout the day, maximizing incident solar radiation. The transmission fibers provide a level of approximately 200 $\mu mol\ m^{-2}s^{-1}$ which prevents photoinhibition and maximizes photon usage efficiency. When there are no available solar photons, the secondary source of light, an artificial source, can be used, thereby allowing for production at all times. Such light sources are conventional for bioreactors.

The ends of the fibers are mounted where the algae move close to the light and away from it in about one half second. Of course, this timing can be modified according to flow rate, pressure and other parameters. Furthermore, the fibers can influence the flow of the water. Therefore, it may be desirable to locate the fibers in the container where it is desirable to have a region of little to no flow (a "dead zone") so that the algae is driven upwardly by the injected gas, and then flows downwardly when the energy of the gas is lost or suitably diminished.

It is preferred for the fibers to possess a hydrophobic nature, that is, the fibers should reject adhesion to the fibers by water molecules. This characteristic reduces the ability of algae to adhere to the surface of the fibers where light is projected out. While this characteristic is common in many plastics, thereby making plastic fibers an attractive alternative to glass, it may not be as easily accomplished with glass fibers. Thus, algae will undoubtedly attach to the ends of the fibers where the light projects. Therefore, it is desirable that there be some action that detaches the algae from the fibers. In the preferred reactor configuration, as noted above, fibers are agitated by the flow of water, and the hanger permits, and even encourages, the fibers to contact the sidewalls of the container. This contact creates an impulse at impact that will detach any algae attached to the fiber.

Three types of algae that are contemplated for use in the bioreactor are AMPHO 46 (Amphora (diatom)), OOCYS 09 (Oocystis (green algae, Chlorophyta)) and SYNEC 05 (Synecococcus (cyanobacterium)). Of course, it is contemplated that other, naturally-existing microorganisms can be used, and that organisms can be modified to work more effectively. For the production of biofuels, such as biodiesel, it is desirable to use algae that produces the most lipids as fast as is feasible. Of course, for the production of other nutraceuticals, pharmaceutical compound or other nutritional compounds, different microorganisms are contemplated. For the production of ethanol and butinol, among others, high starch microorganisms may be more desirable.

The bioreactor has maximum algal productivity for the purpose of producing a high-lipid feedstock for biodiesel refining. Of course, the algae or other photosynthetic microorganism can be used for other purposes, including, but not limited to, other biofuels, nutrition and carbon sequestration. The bioreactor takes advantage of distributed solar energy to maximize productivity during the daylight, and offers the possibility of employing artificial lighting to increase productivity during times without adequate solar energy. The system also minimizes heat dissipation problems from the fiber optics.

The bioreactor has many advantageous features. It can take in a gas from many sources and convert it at high rates to other, more desirable gases, with little to no negative environmental impact. Indeed, the environmental impact may be positive, as in the case of carbon sequestration. As an additional example, the bioreactor can be part of a carbon dioxide recycling system, for example to produce oxygen where it is in short supply. The bioreactor also produces substantial amounts of photosynthetic microorganisms, also with no negative environmental impact. Such organisms can be used for many purposes, such as for animal feed, in the gasification of coal to make hydrocarbon wax and jet fuel, and as otherwise noted herein.

The size of the reactor discussed above is important, although other sizes are contemplated. There must be regions in the container in which the slurry recirculates. If the container is substantially larger than that discussed above, the fluid transport characteristics may not increase, and may even worsen without a substantial modification of the gas injection apparatus. In a preferred embodiment, there is a substantial amount of gas moving through a small diameter container so the gas lifts all the algae/water slurry as the gas flows upwardly. Of course, one could accomplish this by adding nozzles along the height of the container 20. For example, one contemplated alternative embodiment has a nozzle that is substantially identical to the nozzle 30 beneath every hanger. Thus, if the hangers are spaced 24 inches vertically, then the nozzles are also spaced every 24 inches, and 12 inches from the next adjacent hanger. This would form multiple recirculation zones within the container 20. It is most desirable to have continuous, consistent flow to circulate the mixture as much as possible.

In the preferred embodiment, the algae can contact the hangers where the fibers are held in place. The gas flows upwardly at the nozzle openings and continues upwardly around the outside of the container 20. However, the gas has lost much of its energy by the time it reaches the hanger and it therefore ceases to fluidize the algae. Thus, when the algae flows above the hangers it starts to circulate back down again, desirably around the interior of the container 20, as shown by arrows in FIG. 5.

Figure 7:
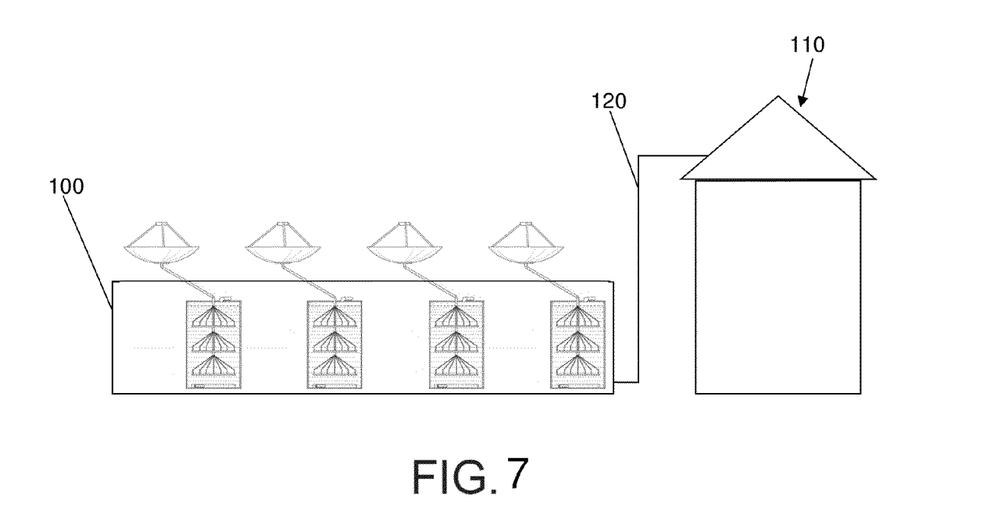
FIG. 7 is a side schematic view illustrating a housing filled with bioreactors that receive gas from a power plant.

In one contemplated embodiment of the invention, a building or other housing 100 is filled with bioreactors similar to the apparatus 10 of the present invention. Thus, a large room contains multiple containers similar to the container 20, each of which has a bundle of optical fibers leading to an external source of light, such as a collector on the roof of the building. One or multiple collectors convey solar radiation through the fibers to each of the bioreactors. Each such bioreactor receives a portion of the $CO_2$-laden gas coming from a source, such as a power plant's 110 exhaust stack 120, and each bioreactor functions as described above to remove $CO_2$ from the gas. Thus, with enough of the bioreactors, a system can receive the millions of cubic feet per hour that a power plant produces. Such bioreactors are spaced apart as much as necessary to provide the microorganisms with the right environment for growth.

The container size is a function of the fluid dynamics, the desired efficiency and pressure of the gas being injected. The optimal tube diameter is a function of the input gas pressure and its volumetric flow rate. For example, in the preferred embodiment, it has been determined that the bulk flow of gas at the point of injection is optimal between about 2 and about 4 meters per second. Of course, this amount can be varied while still achieving some algal growth.

This detailed description in connection with the drawings is intended principally as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention and that various modifications may be adopted without departing from the invention or scope of the following claims.

The invention claimed is:

1. A bioreactor apparatus comprising:
   (a) a container having sidewalls, a floor and a ceiling defining a chamber housing a mixture of liquid growth media and photosynthetic microorganisms;
   (b) a plurality of optical fibers, each of the fibers having a first end disposed outside the chamber and a second end disposed in the mixture, the second end having a tip from which a light beam exits the fiber, wherein the tip of the second end of each fiber is the only region of the fiber in the mixture from which a substantial amount of light exits;
   (c) a light collector spaced from the container, the light collector having light incident thereon and focusing the light onto the first ends of the plurality of optical fibers; and
   (d) at least one nozzle in fluid communication with a source of gas containing at least carbon dioxide, the nozzle disposed in the mixture beneath the second ends of the optical fibers for injecting the gas into the mixture and causing microorganisms to flow from darker regions spaced from the second ends of the fibers and along sides of fibers to the second ends of the fibers and thereby be exposed to light exiting the second ends of the fibers.

2. The bioreactor apparatus in accordance with claim 1, further comprising a hanger mounted to the container sidewalls and through which the second ends of the optical fibers extend for spacing the second ends of the fibers apart laterally and for stabilizing the fibers.

3. The bioreactor apparatus in accordance with claim 1, wherein said at least one nozzle further comprises a first nozzle disposed at one region of the chamber, and a second nozzle disposed at a second, higher region of the chamber, wherein the first nozzle is below at least some of said second ends of the fibers and the second nozzle is above the first nozzle and below at least some of the second ends of the fibers.

4. The bioreactor apparatus in accordance with claim 2, wherein the hanger maintains the second ends of the fibers at a substantially fixed axial position.

5. A method of growing microorganisms, the method comprising:
   (a) disposing a liquid growth media and photosynthetic microorganism mixture in a container having sidewalls and a floor defining a chamber;
   (b) exposing to light a plurality of first ends of a plurality of light-transmitting fibers, wherein said first ends are outside the chamber;
   (c) extending a plurality of second ends of the light-transmitting fibers into the mixture, wherein the second ends have tips that are the only regions of the fibers in the mixture from which a substantial amount of light exits to transmit the light to the chamber, thereby creating light regions in the chamber at the tips of the second ends of the fibers;
   (d) disposing a nozzle in the mixture beneath the second ends of the light-transmitting fibers; and
   (e) injecting gas that is at least partially absorbed by the microorganisms, through the nozzle into the mixture, the injected gas causing microorganisms to flow between light regions, which are substantially only near the second ends, and darker regions, which are spaced from the second ends of the fibers and along sides of the fibers.

6. The method in accordance with claim 5, further comprising stabilizing at least a portion of said at least one light-transmitting fiber relative to the container.

7. The method in accordance with claim 5, further comprising disposing a light collector outside the chamber, focusing the light on the first end of said at least one light-transmitting fiber and displacing the light collector to maximize incident light thereon.

8. The method in accordance with claim 5, further comprising disposing a first nozzle at one region of the chamber, and a second nozzle at a second, higher region of the chamber.

9. The method in accordance with claim 5, wherein the step of injecting the gas further comprises displacing the fiber laterally, thereby causing the second end thereof to contact the sidewall.

10. The method in accordance with claim 5, the method comprising disposing the container within a housing.

11. The bioreactor apparatus in accordance with claim 1, further comprising a power generating apparatus that has a housing and creates exhaust gas from combustion of fossil fuel, and wherein the container is disposed within the housing.

12. The bioreactor in accordance with claim 11, further comprising:
   (a) a plurality of containers having sidewalls, a floor and a ceiling defining a chamber housing a slurry of water and photosynthetic microorganisms, each of said containers disposed within the housing; and
   (b) a plurality of nozzles in fluid communication with the exhaust gas, one of said nozzles disposed in each of the containers, the nozzles injecting the exhaust gas into the mixture of a respective container.

* * * * *